United States Patent [19]
Drain et al.

[11] Patent Number: 5,953,954
[45] Date of Patent: Sep. 21, 1999

[54] INSTALLATION AND METHOD FOR DETERMINING THE LEVEL AND DENSITY OF A LIQUID IN A TANK, USING A SINGLE IMMERSED BUBBLE PROBE

[75] Inventors: François Drain, Saint Nom la Breteche; Jacques Gagniere, Acheres, both of France

[73] Assignee: Compagnie Generale des Matieres Nucleaires, Velizy-Villacoublay, France

[21] Appl. No.: 09/082,839

[22] Filed: May 21, 1998

[30] Foreign Application Priority Data

Jun. 2, 1997 [FR] France ................................. 97 06740

[51] Int. Cl.⁶ .............................. G01F 23/00; G01N 9/00
[52] U.S. Cl. .................................. 73/302; 73/301; 73/439
[58] Field of Search .............................. 73/299, 300, 301, 73/302, 303, 438, 439, 32 R

[56] References Cited

U.S. PATENT DOCUMENTS

| | | | |
|---|---|---|---|
| 3,680,579 | 8/1972 | Hisada et al. | 73/302 |
| 4,215,574 | 8/1980 | Godeux | 73/307 |
| 4,422,327 | 12/1983 | Anderson | 73/303 |
| 4,567,761 | 2/1986 | Fajeau | 73/299 |
| 4,711,127 | 12/1987 | Häfner | 73/302 |
| 5,163,324 | 11/1992 | Stewart | 73/301 |
| 5,406,828 | 4/1995 | Hunter et al. | 73/4 R |
| 5,517,869 | 5/1996 | Vories | 73/865.2 |

FOREIGN PATENT DOCUMENTS 1429352  5/1966  France .

OTHER PUBLICATIONS

Patent Abstracts of Japan, vol. 017, No. 654 (P–1653), Dec. 3, 1993 & JP 05 215660 A (Hitachi Ltd;Others:01), Aug. 24, 1993, Figure 1.
Cousins T: "Fluid Density Measurement"/Measurement and Control, vol. 25, No. 10, Dec. 1992, pp. 292–296, XP000322332, * p. 293, column 1, line 59–column 2, line 21; figure 1.

*Primary Examiner*—Hezron Williams
*Assistant Examiner*—Helen C. Kwok
*Attorney, Agent, or Firm*—Pearne, Gordon, McCoy & Granger LLP

[57] ABSTRACT

An installation and method for determining the level and density of a liquid in a tank. A reference probe leads into the tank, above the liquid. A single bubble probe is connected by a valve to the reference probe. The bubble probe extends into the tank and has a widened section disposed in the liquid. Compressed air is injected into the reference probe and the bubble probe. In an initial state, the valve is opened and there is no pressure difference between the reference probe and the bubble probe. The valve is then closed and the pressure difference between the reference probe and the bubble probe is measured. The level and density of the liquid is determined from measured values of the pressure difference.

9 Claims, 3 Drawing Sheets

INSTALLATION AND METHOD FOR DETERMINING THE LEVEL AND DENSITY OF A LIQUID IN A TANK, USING A SINGLE IMMERSED BUBBLE PROBE

BACKGROUND OF THE INVENTION

The invention relates to an installation designed to determine the level and density of a liquid contained in a tank, using pressure measurements made by means of a bubble probe immersed in the liquid.

The invention also relates to a measuring method using said installation.

The installation and method of the invention find special application in the nuclear industry in order to conduct measurements in tanks containing radioactive solutions.

In the nuclear industry, when it is required to know the level and density of a radioactive solution contained in a tank, a static installation is frequently used such as the one shown in the diagram in FIG. 1 of the appended drawings.

Said installation customarily comprises two immersed bubble probes 1 and 2, dipping vertically into the liquid 3 contained in tank 4, so that their lower ends are positioned at different levels, separated by a distance of height Hd. The installation also comprises a reference probe 5, which leads into tank 4 above the free level of liquid 3. The three probes 1, 2 and 5 are the sole components of the installation located inside the contaminated zone.

Outside this zone, the installation comprises three flowmeters 6, 7 and 10, of variable section, through which each of bubble probes 1, 2 and 5 is supplied with compressed air at a slow flow rate and at a pressure of approximately 1.4 bars.

Finally, outside the contaminated zone, the installation comprises two pressure transmitters 8 and 9 and a calculator (not shown). Pressure transmitter 8 measures the pressure difference Pd between the immersed bubble probes 1 and 2, while pressure transmitter 9 measures the pressure difference Pn between immersed bubble probe 2 and reference probe 5. The calculator receives the pressure signals emitted by pressure transmitters 8 and 9 and calculates the density D of liquid 3, and the level N of this liquid, that is to say the distance of the latter above the bottom of tank 4, using the following equations:

$$D = \frac{Pd}{Hd} \text{ and}$$

$$N = \frac{Pn}{D} + Ho$$

in which Ho represents the height of the lower end of immersed bubble probe 2 above the bottom of tank 4.

Such measuring installations are frequently used and operate in satisfactory manner. However, their extended use has brought to light a certain number of disadvantages.

Firstly, having two bubble probes immersed into the liquid contained in the tank raises a problem of congestion as the inner space of liquid storage tanks is often already well taken up. This is particularly frequent in the nuclear industry.

Also, the complete installation is relatively costly since it comprises two immersed bubble probes and two pressure transmitters. Moreover, multiplying the number of components increases maintenance costs and the risks of contamination in the nuclear industry.

SUMMARY OF THE INVENTION

The invention precisely relates to an installation and a method which can be used to determine the level and density of a liquid in a tank, by reducing the amount of equipment present inside the tank and the overall number of installation components, in order, in particular, to reduce the congestion of the installation inside the tank and its overall cost.

This result is obtained by means of an installation for determining the level and density of a liquid contained in a tank, characterized in that it comprises:

- a reference probe leading into the tank, above the liquid
- a single immersed bubble probe dipping into the tank, finishing in the liquid with one lower end and comprising, above this lower end, an immersed part having a wider section over a given height;
- means for injecting compressed air into the reference probe and bubble probe;
- valve forming means able to open and close a through connection between the reference probe and the bubble probe; and
- means for measuring a pressure difference between the reference probe and the bubble probe.

Since this installation comprises a single immersed bubble probe, its space requirement inside the tank is substantially less than in an installation of the prior art. Also, since only one pressure difference needs to be measured, the installation of the invention uses a single pressure transmitter, which further reduces its cost.

When several tanks are under equipressure, the installation may be further simplified. It is possible, in this case, to use a single reference probe leading into one of the tanks for all density and level measurements made in these tanks. The other tanks then only contain a single immersed bubble probe.

Preferably, the valve forming means and the measuring means are controlled by piloting means. With said piloting means it is possible to conduct automatically at least one measuring cycle, starting from an initial state in which the valve forming means are closed. The measuring cycle is set in operation by opening the valve forming means and activating the measuring means, in such manner as to follow the change, in relation to time, in the pressure difference between the reference probe and the immersed bubble probe.

In this case, the piloting means automatically return the installation to the initial state, after the pressure difference has reached a constant value, and they conduct a new measuring cycle after a pre-determined time interval has lapsed in this initial state.

Another object of the invention is a method for determining the level and density of a liquid contained in a tank. This method comprises the following stages:

a: allowing to communicate a reference probe leading into the tank above the liquid, and an immersed probe dipped into the tank finishing at a height Ho in the liquid with its lower end and comprising, above this lower end, an immersed part of widened section over a given height Hd;

b: injecting compressed air simultaneously into the reference probe and the bubble probe and closing the communication between these two probes;

c: measuring the change- in pressure between the reference probe and the bubble probe until a threshold is reached;

d: determining the level N and the density D of the liquid, using values $P_B, P_A$ of the pressure difference measured corresponding respectively to the threshold and to a slope breakpoint using the equations:

$$D = \frac{P_B - P_A}{Hd} \text{ and}$$

$$N = \frac{P_B}{D} + Ho$$

$P_B$ corresponding to the pressure difference measured between points B and C, and $P_A$ relating to the pressure difference between points A and C.

Stages a, b, c and d are renewed in cyclical manner when a predetermined time interval (for example one minute) has lapsed after reaching a threshold.

Analysis of the signal representing the change in pressure difference measured during stage c, that is to say when the liquid falls in the bubble probe, can detect any possible disturbance of this signal. Such disturbance, characterized by irregularities in the pressure rise curve, might be attributable to discontinuities in the pipe section resulting from the onset of crystallization or deposit in the probe. It is therefore possible to detect any onset of clogging.

With early detection of the onset clogging, said clogging can be avoided by rinsing the bubble probe.

BRIEF DESCRIPTION OF THE DRAWINGS

A description is given below, as a non-restrictive illustration, of a preferred embodiment of the invention with reference to the appended drawings in which.

DETAILED DESCRIPTION OF THE PREFERRED EMBODIMENTS

Figure 2:
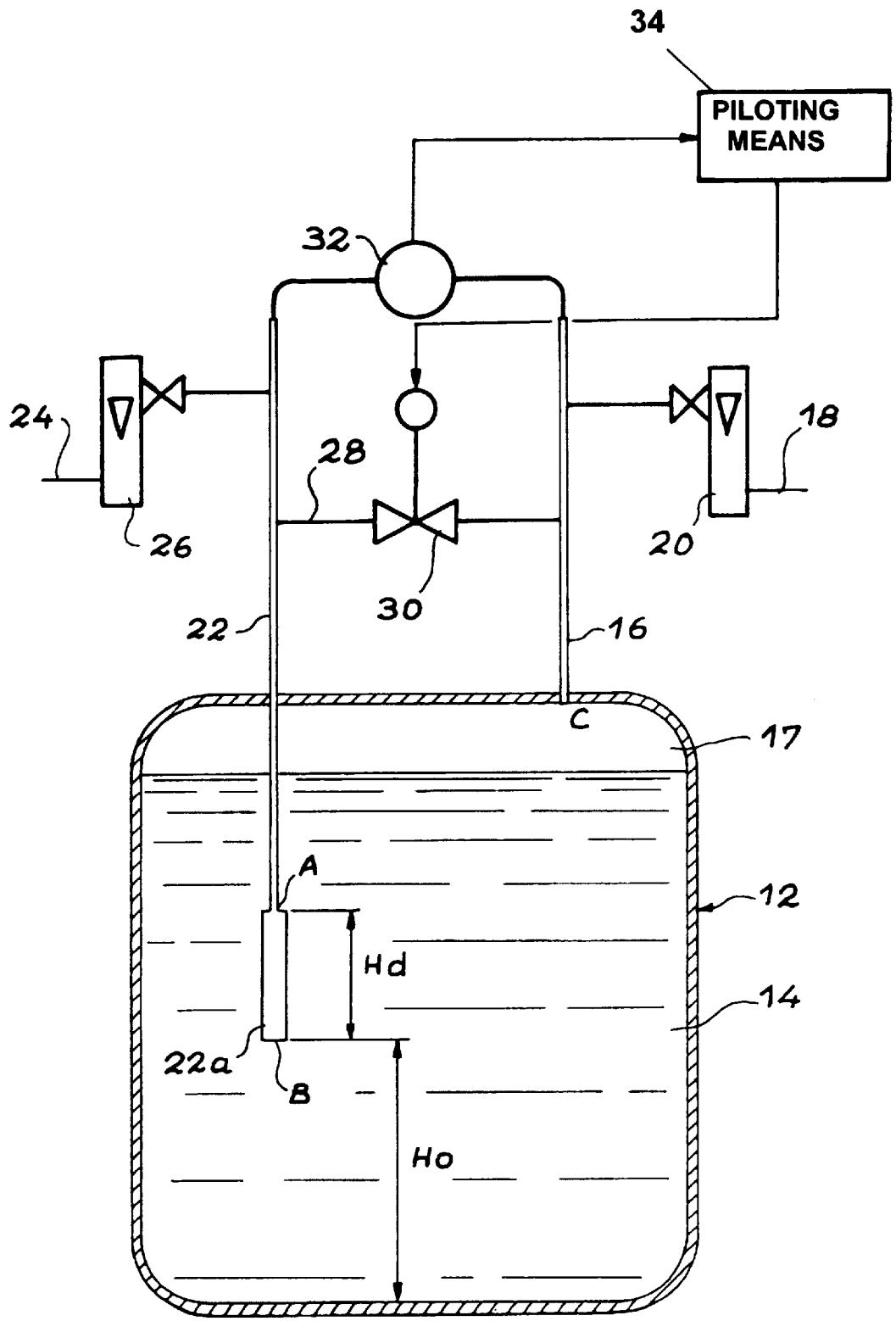
FIG. 2 is a similar view to FIG. 1, illustrating an installation in accordance with the invention, which can be used to determine the level and density of a liquid contained in a tank.

In FIG. 2, reference 12 refers to a tank containing a liquid 14 whose level and density are to be measured. Tank 12 may, in particular, be a storage tank used in the nuclear industry. In this case, liquid 14 is a radioactive solution and the tank marks the boundary of a contaminated zone.

In accordance with the invention, the density D of the liquid 14 and its level N inside tank 12 are determined using an original, particularly simple, installation that is not expensive and requires limited space.

This installation comprises a reference probe 16, leading into tank 12, above liquid 14. Reference probe 16 is in the form of a pipe of uniform section, vertically connected on the upper wall of the tank, so that it ends at C in the dome of tank 17 above liquid 14. At its opposite end, located outside tank 12, reference probe 16 is connected to a compressed air source (not shown) by piping 18. A flowmeter 20 of variable section is placed in piping 18, in order to limit the flow of compressed air entering reference probe 16 to a relatively low rate (for example, approximately 6 Nl/h) and to a pressure of approximately 1.4 bars.

In accordance with the invention, the installation also comprises a single immersed bubble probe 22, which dips vertically into tank 12 so that it finishes in liquid 14 with its lower end B. More precisely, immersed bubble probe 22 is made up of a pipe which has a uniform section over its entire length, with the exception of a lower immersed part 22a, of wider section. Since immersed bubble probe 22 is vertical, the length of the immersed part 22a corresponds to a height Hd inside tank 12. It is to be noted that the upper end A of immersed part 22a of immersed bubble probe 22 is positioned at a level such that said part 22a always remains fully immersed in liquid 14.

Outside tank 12, immersed bubble probe 22 is connected to a compressed air source (not shown) by piping 24. A flowmeter 26 of variable section, similar to flowmeter 20, is placed in said piping 24 in order to limit the flow of compressed air entering immersed bubble probe 22 to a relatively low rate (for example approximately 6 Nl/h) and to a pressure of approximately 1.4 bars.

The installation in accordance with the invention also comprises, outside tank 12, a diversion pipe 28 connecting reference probe 16 to immersed bubble probe 22. Valve forming means 30, such as an electrovalve, are placed in this diversion piping 28. When valve forming means 30 are closed, probes 16 and 22 are insulated from each other. On the other hand, the two probes communicate with one another when valve forming means 30 are open.

The installation in accordance with the invention also comprises measuring means 32, also placed outside tank 12. These measuring means 32 are made up of a differential pressure transmitter. They are placed between reference probe 16 and immersed bubble probe 22, so that they measure in real time the pressure difference these two probes.

Finally, the installation advantageously comprises, outside tank 12, piloting means 34 including for example an automaton and a calculator. These piloting means 34 provide control over valve forming means 30 and measuring means 32. Also, they receive the signals issued by measuring means 32, representing the instant pressure difference between reference probe 16 and immersed bubble probe 22. As will be explained in more detail below, piloting means 34 are to used to operate the conduction of measuring cycles at regular time intervals.

Figure 1:
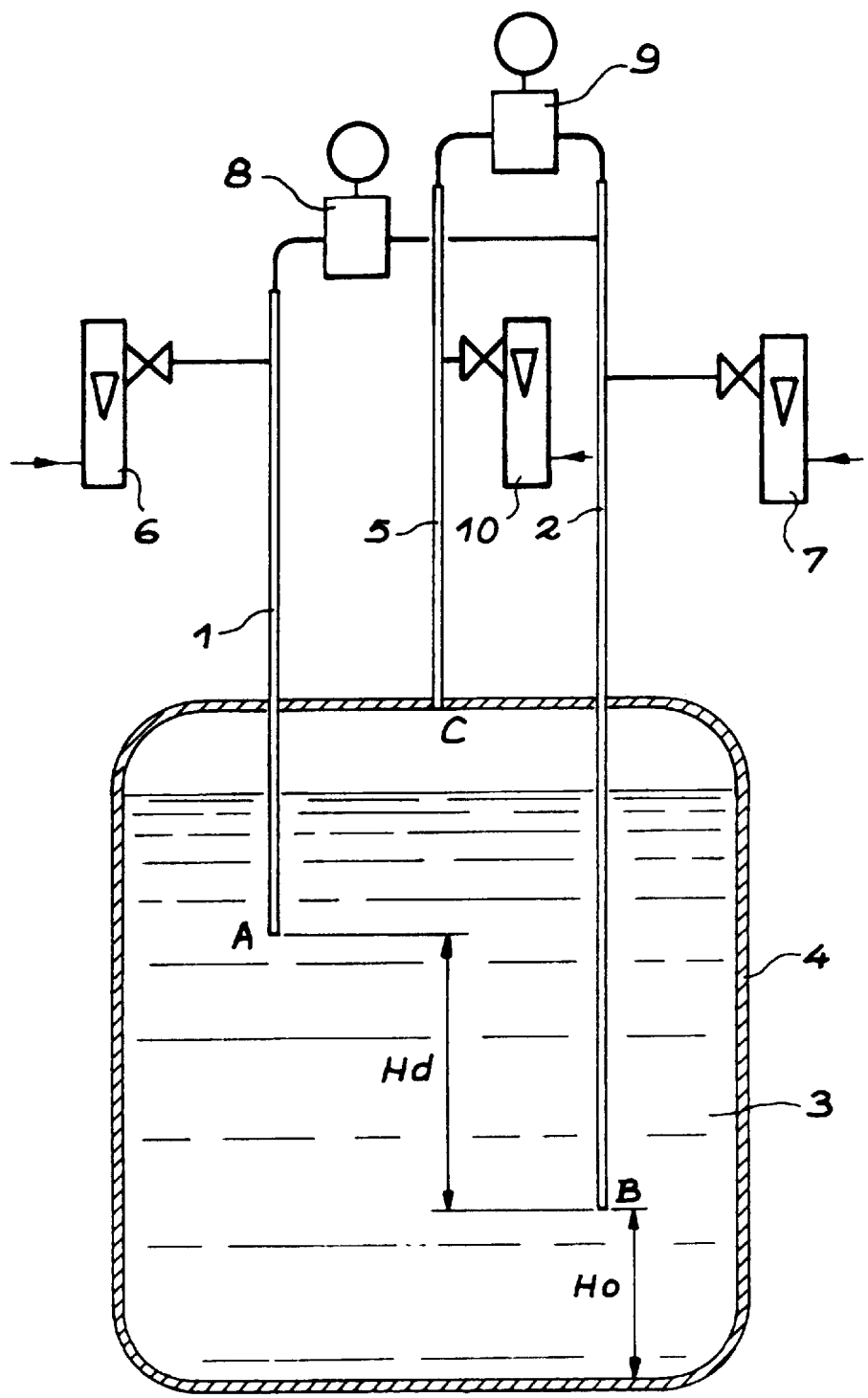
FIG. 1, already described, is a diagram of an installation of the prior art used to determine the level and density of a liquid contained in a tank.

The advantages offered by the installation of the invention are immediately apparent from a comparison between FIG. 2, giving a diagram of the installation, and FIG. 1, giving a diagram of an installation of the prior art.

It will be observed that with the installation of the invention only one immersed bubble probe needs to be placed inside tank 12, instead of two in existing installations. The space taken up inside the tank is therefore much reduced, which is a notable advantage, especially in the nuclear industry where a great number of equipment parts are often present inside storage tanks.

The comparison between FIGS. 1 and 2 also shows that the installation of the invention allows the number of equipment parts forming the installation to be substantially reduced. The number of bubble probes and pressure transmitters is reduced by half compared with installations of the prior art. The cost of the installation is thereby reduced as well as maintenance costs. Also there is a reduced risk of contamination.

A further advantage of the installation of the invention arises from the possibility of automatic piloting of measuring cycles, at regular intervals, using piloting means 34 in the manner described below.

When the installation of the invention is set in operation, piloting means 34 bring the installation fiercely to an initial state, in which compressed air at a set flow rate and pressure is injected both into reference probe 16 and into immersed bubble probe 22 through flowmeters 20 and 26 respectively. In this initial state, valve forming means 30 are open, so that probes 16 and 22 communicate with one another. Under these conditions, the compressed air follows the circuit offering the lowest counter-pressure, namely that which leads to the dome of tank 17 through reference probe 16. There is therefore no injection of air into immersed bubble probe 22. Measuring means 32 do not then detect any difference between probes 16 and 22.

When a measuring cycle is set in operation, preferably automatically, by piloting means 34, the valve forming means 30 are closed and the injection of compressed air through flowmeters 20 and 26 is continued. Immersed bubble probe 22 is then placed under pressure and the liquid it contains is gradually expelled.

Figure 3:
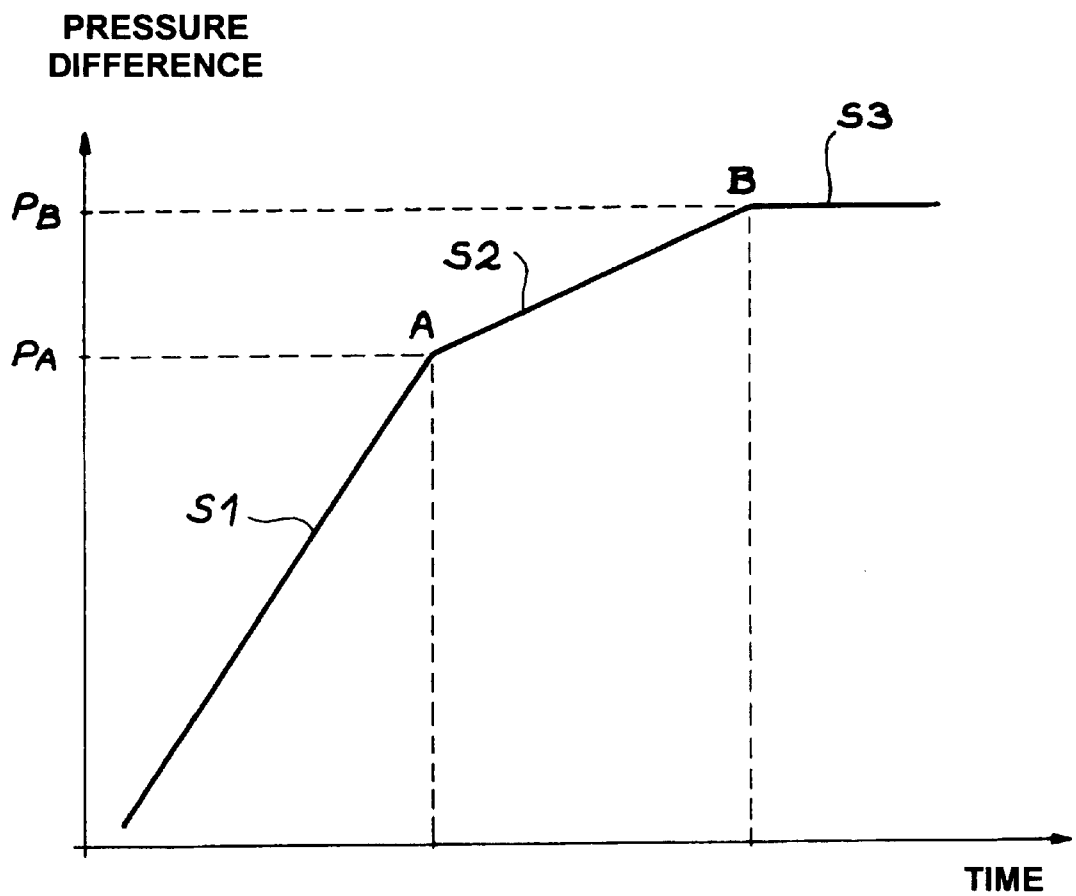
FIG. 3 is a graph showing the change in pressure difference between the reference probe and the immersed probe, in relation to time, when a measuring cycle is performed by the installation in FIG. 2.

As is illustrated by segment S1 in FIG. 3, representing the change in relation to time of the pressure difference measured by measuring means 32, this pressure difference first increases fairly rapidly as long as the level of liquid in immersed bubble probe 22 remains higher than that of the upper end A of immersed part 22a of this probe.

As soon as the level of liquid reaches this upper end A, the curve representing the measured change in pressure difference in relation to time shows a slope breakpoint beyond which the curve is less inclined. Therefore, as long as the level of liquid inside immersed bubble probe 22 remains inside immersed part 22a of wider section, the pressure difference measured by measuring means 32 follows segment S2 in FIG. 3.

Finally, when the liquid is fully expelled from immersed bubble probe 22, the pressure difference measured by measuring means 32 reaches a constant value which corresponds to segment S3 of the curve in FIG. 3.

By conducting this measuring cycle, it is therefore possible to determine the pressure difference values $P_A$ and $P_B$ which respectively correspond to the crossing of upper end A and lower end B of immersed part 22a of immersed bubble probe 22, when the liquid is gradually expelled from this probe by air. In the curve in FIG. 3, pressure $P_A$ corresponds to the slope breakpoint between segments S1 and S2, and pressure $P_B$ corresponds to the threshold represented in segment S3.

When this threshold is reached, piloting means 34 automatically return the installation to its initial state, by opening valve forming means 30. The air contained in immersed bubble probe 22 is then expelled into the dome of tank 17 through diversion pipe 28 and reference probe 16.

A new measurement can then be set in operation by piloting means 34 in such manner as to obtain a predetermined cycle of measurements which may, as an example that is in no way restrictive, last approximately 1 min.

At the end of each measurement cycle, piloting means 34 determine level N and density D of liquid 14 contained in tank 12. More precisely, density D of liquid 14 is calculated using the equation:

$$D = \frac{P_B - P_A}{Hd}$$

Also, level N of liquid 14 in tank 12, that is to say the height of the liquid above the bottom of this tank, is calculated using the equation:

$$N = \frac{P_B}{D} + Ho$$

in which Ho represents the height of lower end B of immersed part 22a of immersed bubble probe 22, that is to say the distance separating this lower end from the bottom of tank 12.

In the installation that has just been described, liquid 14 regularly rises in bubble probe 22 at regular periods of, for example, one minute. This has a rinsing effect but also brings a risk of clogging through crystallisation or deposit in the probe.

However, the onset of crystallisation or deposit in immersed probe 22 leads to disturbance of the signal representing the change in pressure difference measured when the liquid falls in the probe. Since the pipe section is no longer continuous, the pressure rise curve then shows irregularities.

Consequently, analysis of the above cited signal can be used to detect any disturbance in the latter, representing the onset of clogging in bubble probe 22.

Under these conditions, that is to say on early detection of the onset of clogging, preventive rinsing of bubble probe is carried out to avoid its clogging.

When the installation of the invention is used in the nuclear industry, it is to be noted that measuring means 32 carry no risk of being contaminated by the radioactive solution contained in the tank. These measuring means 32 are insulated from the air rising from probe 22 through the slow flow, continuous injection of compressed air in each of these probes through flowmeters 20 and 26.

Also, should the installation of the invention be intended to carry out measurements simultaneously on several tanks under equipressure, that is to say whose tank domes communicate with one another, it is possible to further simplify the installation for each of these tanks by using a single reference probe 16 for all the tanks. In other words, only one of these tanks is fitted with a reference probe 16 and an immersed bubble probe 22, all the other tanks simply comprising one immersed bubble probe.

While the installation of the invention is particularly adapted for use in the nuclear industry, it may also be applied to other industries, to all situations with tanks containing dangerous products.

Finally, it will be noted that the means of injecting compressed air into the probes, the valve forming means, and the measuring means may be in different forms to those described while remaining within the limits of the invention. In similar spirit, the piloting means may in some cases be omitted or simplified, certain operations, and also measurements and calculations in this case possibly being conducted manually.

We claim:

1. Installation for determining the level and density of a liquid contained in a tank, said installation comprising:
    a reference probe leading into the tank, above the liquid;
    a bubble probe connected to the reference probe, said bubble probe extending into the tank and terminating at a lower end disposed in the liquid, said bubble probe comprising a widened section disposed in the liquid, above the lower end, and having a height (Hd):
    means for injecting compressed air into the reference probe and the bubble probe;
    a valve for controlling fluid flow between the reference probe and the bubble probe; and
    means for measuring a pressure difference between the reference probe and the bubble probe.

2. Installation in accordance with claim 1, wherein the installation is operable to determine the level and density of liquid contained in at least a second tank, and wherein the installation further comprises a second bubble probe disposed in the second tank.

3. Installation in accordance with claim 1, in which the bubble probe extends vertically in the liquid in the tank.

4. Installation in accordance with claim 1, wherein the valve and the measuring means are operated by piloting means for performing at least one measuring cycle, starting from an initial state in which the valve is open, said measuring cycle including closing the valve and starting the measuring means in order to follow the change, in relation to time, in the pressure difference between the reference probe and the bubble probe.

5. Installation in accordance with claim 4, in which the piloting means automatically return the installation to said initial state, after said pressure difference has reached a constant value, and perform a new measuring cycle when a pre-determined time interval has lapsed in said initial state.

6. Method for determining the level and density of a liquid contained in a tank, said method comprising the steps of:

a—providing a reference probe leading into the tank, above the liquid, and a bubble probe communicable with the reference probe, said bubble probe extending into the tank and terminating at a lower end disposed in the liquid at a height Ho, said bubble probe comprising a widened section disposed in the liquid, above the lower end, and having a height Hd;

b—injecting compressed air into the reference probe and the bubble probes;

c—closing communication between the reference probe and the bubble probe;

d—measuring values of a pressure difference between the reference probe and the bubble probe, until a threshold is reached;

e—determining the level N and density D of the liquid, on the basis of measured pressure difference values $P_A$ and $P_B$ corresponding respectively to the threshold and a slope breakpoint using the equations:

$$D = \frac{P_B - P_A}{Hd} \text{ and}$$

$$N = \frac{P_B}{D} + Ho$$

7. Method in accordance with claim 6, in which, after reaching the threshold, the reference probe and the bubble probe are again allowed to communicate, and a new cycle is performed including steps b, c and d after a pre-determined time interval has lapsed.

8. Method in accordance with claim 7, in which a signal representing the change in pressure difference measured during step c is analyzed to detect any possible disturbance of the signal, representing the onset of clogging in the bubble probe.

9. Method in accordance with claim 8, in which the bubble probe is rinsed when the onset of clogging is detected.

* * * * *

UNITED STATES PATENT AND TRADEMARK OFFICE
CERTIFICATE OF CORRECTION

PATENT NO. : 5,953,954
DATED : September 21, 1999
INVENTOR(S) : Francois Drain et al.

It is certified that error appears in the above-indentified patent and that said Letters Patent is hereby corrected as shown below:

Column 3, line 21, after "onset" insert therefore --of--.

Column 7, line 31, claim 6, delete "probes" and insert therefore --probe--.

Signed and Sealed this

Eighteenth Day of April, 2000

Attest:

Q. TODD DICKINSON

*Attesting Officer*     *Director of Patents and Trademarks*